United States Patent [19]

Azar

[11] Patent Number: 5,759,200
[45] Date of Patent: Jun. 2, 1998

[54] METHOD OF SELECTIVE PHOTOTHERMOLYSIS

[76] Inventor: Zion Azar, 6 Almog Street, Neve Monosson, Israel

[21] Appl. No.: 707,562

[22] Filed: Sep. 4, 1996

[51] Int. Cl.$^6$ ..................................................... A61N 5/00
[52] U.S. Cl. ............................. 607/89; 606/9; 606/10; 606/11; 606/17; 606/27
[58] Field of Search ..................... 606/9–12, 13, 606/17, 27, 28; 607/1, 88, 89, 90; 128/898

[56] References Cited

U.S. PATENT DOCUMENTS

| | | | |
|---|---|---|---|
| 4,604,992 | 8/1986 | Sato | 600/108 |
| 4,686,986 | 8/1987 | Fenyö et al. | 350/394 |
| 5,071,417 | 12/1991 | Sinofsky | 606/12 |
| 5,312,395 | 5/1994 | Tan et al. | 607/89 |
| 5,441,531 | 8/1995 | Zarate et al. | 607/88 |
| 5,521,392 | 5/1996 | Kennedy et al. | 250/492.1 |
| 5,604,629 | 2/1997 | Hunter et al. | 359/359 |

FOREIGN PATENT DOCUMENTS

WO 91/15264  10/1991  WIPO .

OTHER PUBLICATIONS

McDaniel, D.H., "Cutaneous Vascular Disorders: Advances in Laser Treatment", CUTIS, vol. 45, pp. 339–360, May, 1990.

Hurwitz, R.M. et al, "PortWine Stain: A New Therapeutic Approach to an Old Birth Defect", Indiana Medicine, pp. 336–339, May, 1990.

Tan, O.T. et al, "585nm for the Treatment of Port–Wine Stains", Plastic and Reconstructive Surgery, pp. 1112–1117, Dec. 1990.

Kurban, A.K. et al, "The Importance of Pulse Duration in Laser–Tissue Interactions: A Histological Study".

Anderson, R.R. et al., "Selective Photothermolysis: Precise Microsurgery by Selective Absorption of Pulsed Radiation", Science, vol. 220, pp. 524–527, 29 Apr. 1983.

Internet Web Site for the Institute for Dermatology and Cosmetic Surgery 6 pages.

Candela Corp news release–"Candela Expands Skin Laser Product Line", 4 pages.

Candela Corp website advertizement—2 pages.

U.S. Federal Trade Commission—Website—Varicose Veins Treatment, 4 pages.

*Primary Examiner*—Jennifer Bahr
*Assistant Examiner*—Rosiland Kearney
*Attorney, Agent, or Firm*—Mark M. Friedman

[57] ABSTRACT

A method and device for selective photothermolysis of a surgical target within surrounding tissue. The target and the surrounding tissue are heated to about 60° C. Then the target is heated to the point of coagulation, preferably by monochromatic light. The temperature difference between the coagulating target and the surrounding tissue is sufficiently mild that heat diffusing out of the target does not damage the surrounding tissue, even in the case of a relatively large target such as varicose veins.

13 Claims, 6 Drawing Sheets

METHOD OF SELECTIVE PHOTOTHERMOLYSIS

FIELD AND BACKGROUND

The present invention relates to dermatological surgery and, more specifically, to a method of selective photothermolysis that allows the destruction of targets, such as varicose veins, that are too large to be destroyed by presently known methods without damaging the surrounding healthy tissue.

Selective photothermolysis is a surgical method, introduced by Anderson and Parrish in 1983 ("Selective Photothermolysis: Precise Microsurgery by Selective Absorption of Pulsed Radiation ", Science, Vol. 220, pp.524–527), for destroying certain diseased or unsightly tissue, on or near the skin, with minimal damage to the surrounding healthy tissue. The tissue to be destroyed must be characterized by significantly greater optical absorption at some wavelength of electromagnetic radiation than the surrounding tissue. The method consists of irradiating the target and the surrounding tissue with pulsed electromagnetic radiation, usually visible radiation, that is preferentially absorbed by the target. The energy and duration of the pulses is such that the target is heated to between about 70° C. and about 80° C, at which temperature the proteins of the target coagulate. Because the target absorbs the incident radiation much more strongly than the surrounding tissue, the surrounding tissue is heated negligibly.

Usually, the radiation source is a laser, for example a flashlamp-pulsed dye laser. A laser source has the advantage of being inherently monochromatic. Other sources include broad band sources used in conjunction with narrow band filters, as described, for example, by Gustaffson in Patent No. WO 91/15264. A similar device, called the "Photoderm-VL", is manufactured by ESC Medical Systems.

Suitable targets for selective photothermolysis include birthmarks, port-wine stains, spider veins, and varicose veins, all of which tend to be much redder than the surrounding tissue because of their higher concentration of oxyhemoglobin-containing red blood cells. Anderson and Parrish used light of a wavelength of 577 nanometer, corresponding to the 577 nanometer oxyhemoglobin absorption band. It was subsequently determined (Tian, Morrison, and Kurban, "585 nm for the Treatment of Port-Wine Stains", Plastic and Reconstructive Surgery, vol. 86 no. 6 pp. 1112–1117) that 585 nanometer is a more effective wavelength to use.

One constraint on the pulse duration is that the surrounding tissue must not be heated to the point that it, too, begins to coagulate. As the target is heated, heat begins to diffuse from the target to the cooler surrounding tissue. To keep the surrounding tissue from being heated to the point of damage, the pulse length must be kept on the order of the target's thermal relaxation time. For relatively small targets, such as birthmarks, port-wine stains, and spider veins, typical pulse lengths are on the order of hundreds of microseconds. For varicose veins, pulse lengths on the order of milliseconds should be used.

A complication arises in the treatment of varicose veins by selective photothermolysis. The normal tissue surrounding varicose veins typically includes other blood vessels, notably capillaries, that also absorb the incident radiation but, being much smaller than the varicose veins, have much shorter thermal relaxation times. Therefore, heat diffusing from these other blood vessels into the surrounding tissue tends to heat the surrounding tissue to the point of damage, thereby causing scarring.

There is thus a widely recognized need for, and it would be highly advantageous to have, a method of selective photothermolysis that is effective in removing larger surgical targets, such as varicose veins, without peripheral damage.

SUMMARY OF THE INVENTION

According to the present invention there is provided a method of selective photothermolysis of a target within surrounding tissue, comprising the steps of:
  (a) to heating the target and the surrounding tissue above normal body temperature; and
  (b) heating the target to between about 70° C. and about 80° C.

According to the present invention there is provided a device for selective photothermolysis of a target within surrounding tissue, comprising:
  (a) means for generating broad-band electromagnetic radiation; and
  (b) means for generating at least one pulse of substantially monochromatic electromagnetic radiation, each of said at least one pulse being substantially simultaneous with said broad-band electromagnetic radiation.

The method of the present invention is based on the fact that the rate of heat diffusion from a warm body to a cold body is proportional to the thermal gradient between the bodies. Therefore, heating the surrounding tissue to a temperature higher than normal body temperature, but not high enough to cause damage, and only then heating the target to the point of coagulation, creates an environment in which the thermal gradient between the target and the surrounding blood vessels, on the one hand, and the other surrounding tissue, on the other hand, is sufficiently small that the surrounding tissue is not damaged. In the context of the present invention, "higher than normal body temperature" means a temperature of at least about 40° C., but preferably between about 55° C. and about 65° C. Furthermore, the pulse of monochromatic light used to heat the target may be of lower power and shorter duration than in the prior art, because the target is heated from a higher initial temperature.

The device of the present invention accomplishes this end by heating the surrounding tissue using broad-band electromagnetic radiation. The scope of the present invention includes all effective wavelengths of electromagnetic radiation, and effective spectral bands for this purpose include microwave radiation; but the preferred spectral band, both for heating the surrounding tissue and for heating the target itself is visible radiation. The preferred device for generating the broad-band (white) light is a high intensity lamp such as a xenon arc lamp. The device includes a mechanism for pulsing the light from the lamp. This mechanism may include circuitry for controlling the current supplied to the lamp (e.g., the mechanism may operate by turning the lamp on and off); or may include a mechanical shutter.

There are two preferred means for generating the substantially monochromatic radiation used to heat the target. The first is a laser that operates at the desired wavelength, preferably a wavelength between about 570 nanometer and about 610 nanometer. The second is to pass light from the high intensity lamp through a suitable wavelength selection device, such as a narrow band filter or a monochromator.

The device of the present invention synchronizes the monochromatic pulses with the broad-band electromagnetic radiation, by means well-known in the art, to ensure that the surrounding tissue has been heated sufficiently before the monochromatic pulse is turned on to heat the target further, and to ensure that the target is heated further before the surrounding tissue has a chance to cool down. In general terms, this means that, if the broad-band electromagnetic radiation is pulsed, then each monochromatic pulse is substantially simultaneous with a broad-band pulse. As used herein "substantially simultaneous" means that the monochromatic pulse is turned on either while the broad-band pulse is on, or substantially immediately after the broad-band pulse is turned off.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method and device for selective photothermolysis of relatively large surgical targets. Specifically, the present invention can be used to remove varicose veins and similar diseased or unsightly tissue with minimal damage to the surrounding healthy tissue.

The principles and operation of a method and device for selective photothermolysis according to the present invention may be better understood with reference to the drawings and the accompanying description.

Figure 1:
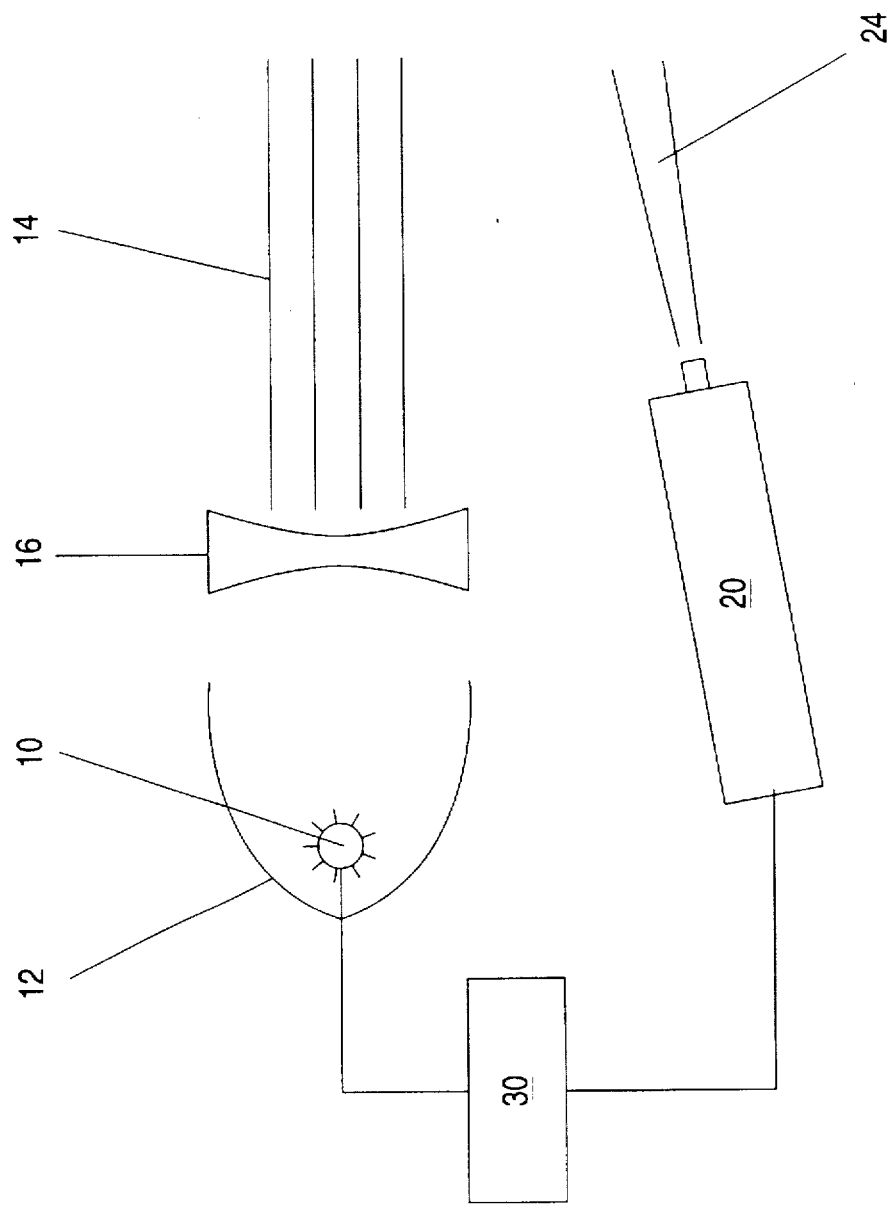
FIG. 1 is a schematic diagram of a preferred embodiment of the device of the present invention in which the source of monochromatic light is a laser.

Referring now to the drawings, FIG. 1 is a schematic diagram of a preferred embodiment of the device of the present invention. A high intensity lamp 10 functions as a source of broad-band (white) light 14. Because lamp 10 emits light in all directions, a parabolic reflector 12 and a concave lens 16 are provided to collimate broad-band light 14, so that substantially all of the energy emitted by lamp 10 is directed at the target and the surrounding tissue. A laser 20 emits substantially monochromatic light 24, preferably at a wavelength of 585 nanometer, also towards the target and the surrounding tissue. A control system 30 supplies power to lamp 10 and laser 20, and also turns lamp 10 and laser 20 on and off in accordance with the pulse schedule shown in FIG. 2.

Preferably, lamp 10 is a xenon arc lamp. Preferably, laser 20 is a flashlamp-pulsed dye laser, for example the Sclero-LASER manufactured by Candela Corporation of Wayland Mass.

Figure 2:
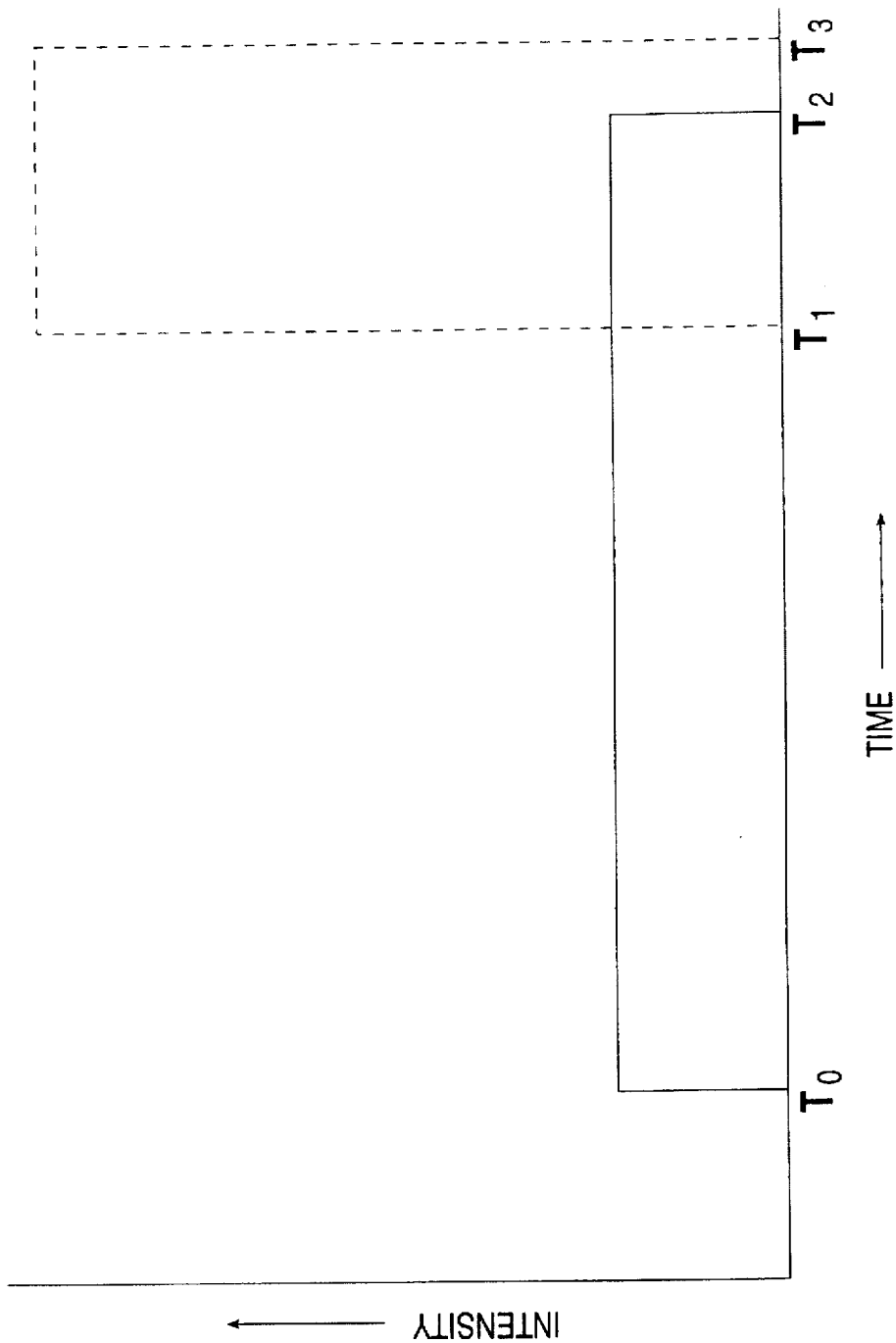
FIG. 2 shows a pulse schedule for the device of FIG. 1.

FIG. 2 shows a pulse schedule for the device of FIG. 1. The solid line in FIG. 2 represents the duration and intensity of a pulse of broad-band light 14. The dashed line in FIG. 2 represents the duration and intensity of a pulse of monochromatic light 24. Broad-band light 14 is turned on at time $T_0$, and is kept on long enough, until time $T_2$, to heat the target and the surrounding tissue to about 60° C. As the temperature of the surrounding tissue approaches the desired final value, monochromatic light 24 is turned on at time $T_1$, and is kept on until time $T_3$, long enough to cause coagulation of the target but not long enough to damage the surrounding tissue. Preferably, the duration of the monochromatic pulse is between about 0.1 milliseconds and about 10 milliseconds.

Figure 3:
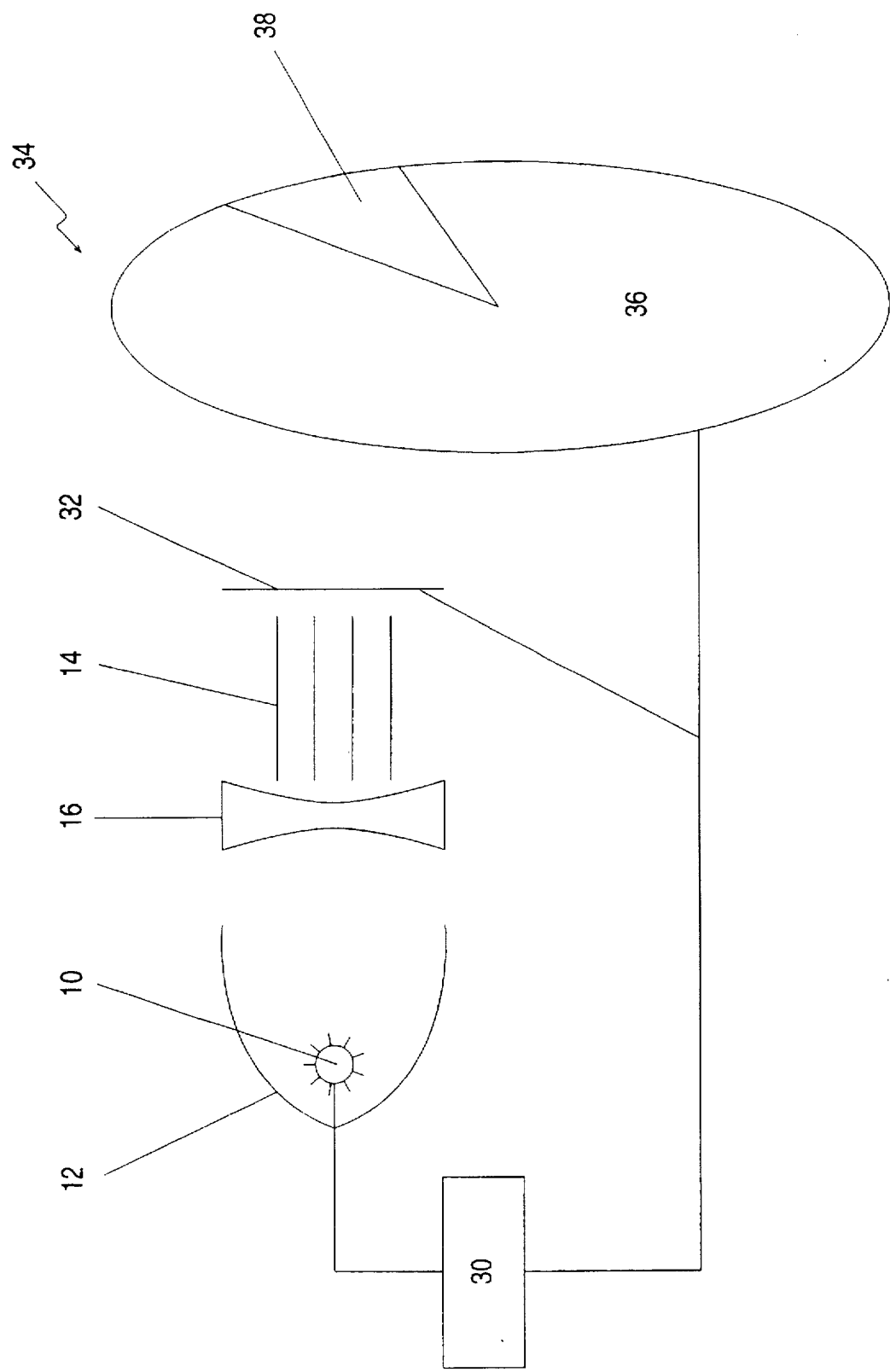
FIG. 3 is a schematic diagram of a preferred embodiment of the device of the present invention in which the source of monochromatic light is the same as the source of the broad-band light.

FIG. 3 is a schematic diagram of another preferred embodiment of the device of the present invention. In this embodiment, lamp 10 serves as the source of both the broad-band radiation and the monochromatic radiation that are incident on the target and the surrounding tissue. In this embodiment, a mechanical shutter 32 serves to alternately block and pass broad-band light 14, thus causing the light emerging from the device to be pulsed. A rotating circular filter 34 having two sections, a white section 36 and a colored section 38, serves to filter the broad-band pulses passed by shutter 32. White section 36 attenuates all wavelengths to substantially the same degree, thereby providing a broad-band pulse of the proper intensity and duration to heat the target and the surrounding tissue to about 60° C. Colored section 38 attenuates all but a narrow spectral band of light centered on a wavelength of 585 nanometer. Control system 30 synchronizes the movement of shutter 32 and filter 34 to provide light pulses according to the pulse schedule of FIG. 4.

Note that lamp 10 must be much more powerful in the embodiment of FIG. 3 than in the embodiment of FIG. 1, because in the embodiment of FIG. 3, lamp 10 must provide enough spectral power in the vicinity of 585 nanometer to coagulate the target. It is for this reason that white section 36 of filter 34 is required in this embodiment.

Figure 4:
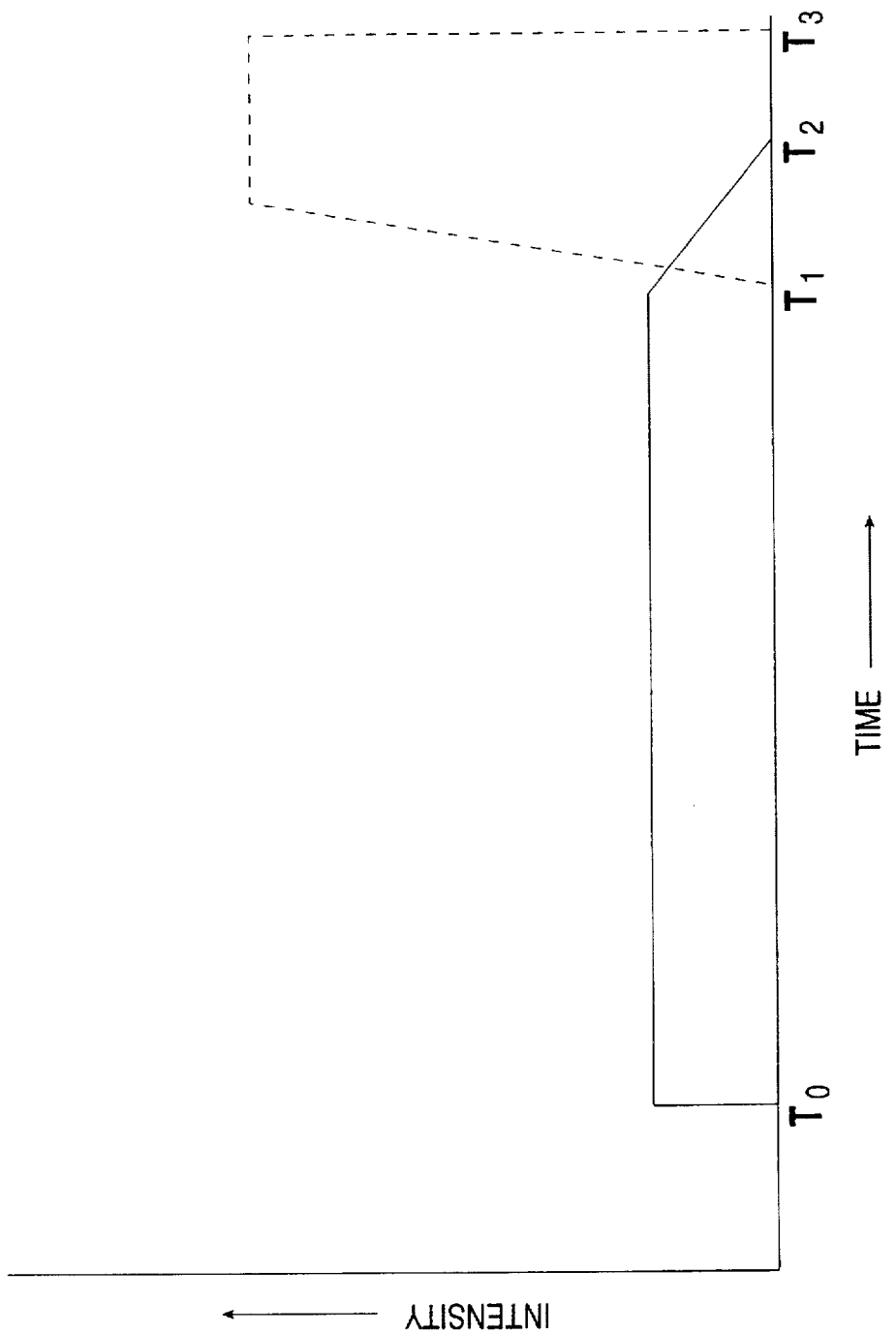
FIG. 4 shows a pulse schedule for the device of FIG. 3.

FIG. 4 shows a pulse schedule for the device of FIG. 3. As in FIG. 2, a solid line represents a broad-band pulse and a dashed line represents a monochromatic pulse. At time $T_0$, with filter 34 positioned so that white section 36 is in the optical path of broad-band light 14, shutter 32 is opened, allowing broad-band light 14 to pass through, and to be attenuated by, white section 36. Filter 34 is rotated, until, at time $T_1$, colored section 38 begins to intercept broad-band light 14. At time $T_2$, all of broad-band light 14 is passing through colored section 38, so that the light emerging from the device is substantially monochromatic. At time $T_3$, shutter 32 is closed, terminating the monochromatic pulse.

Figure 5:
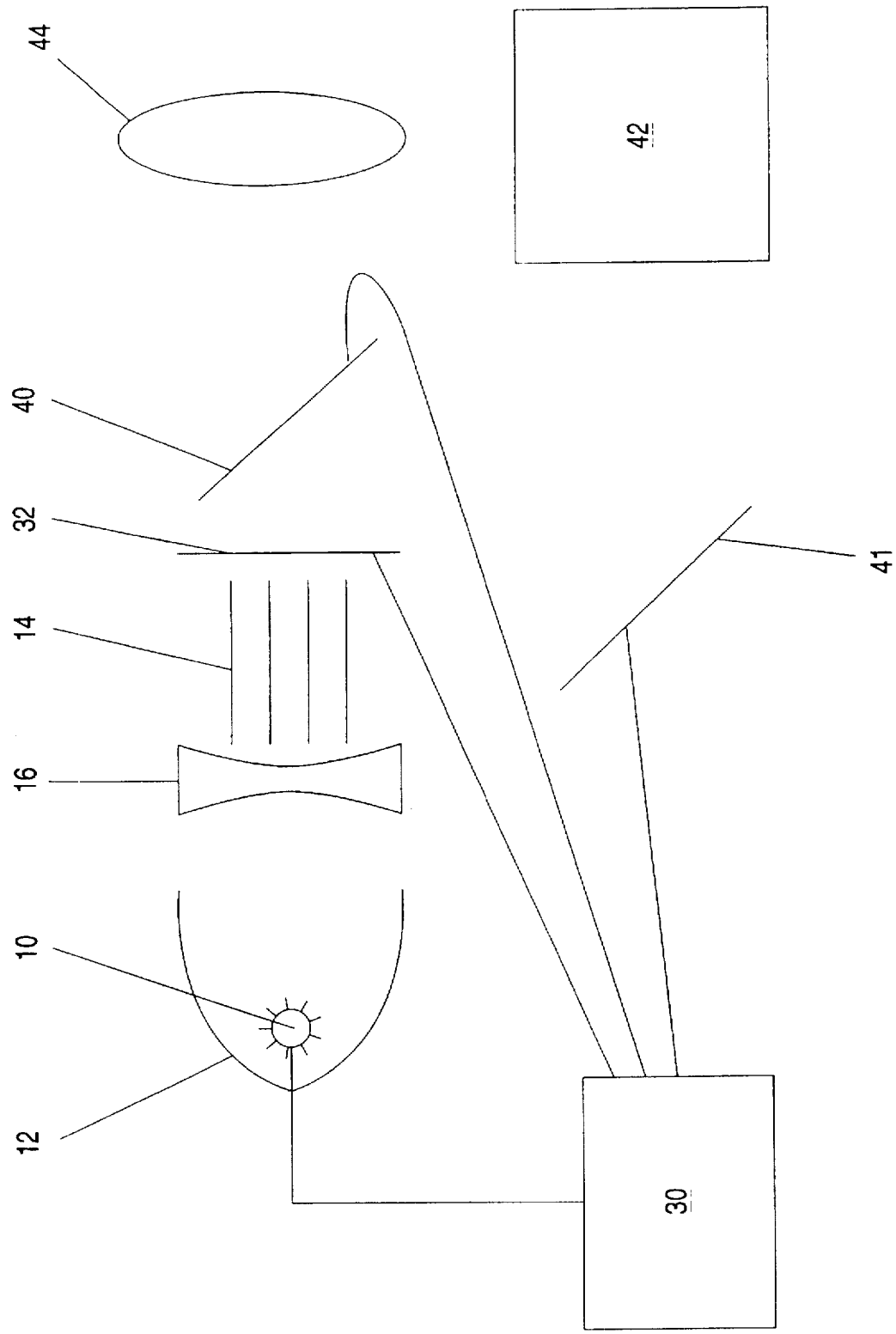
FIG. 5 shows an alternative embodiment of the device of FIG. 4.
Figure 6:
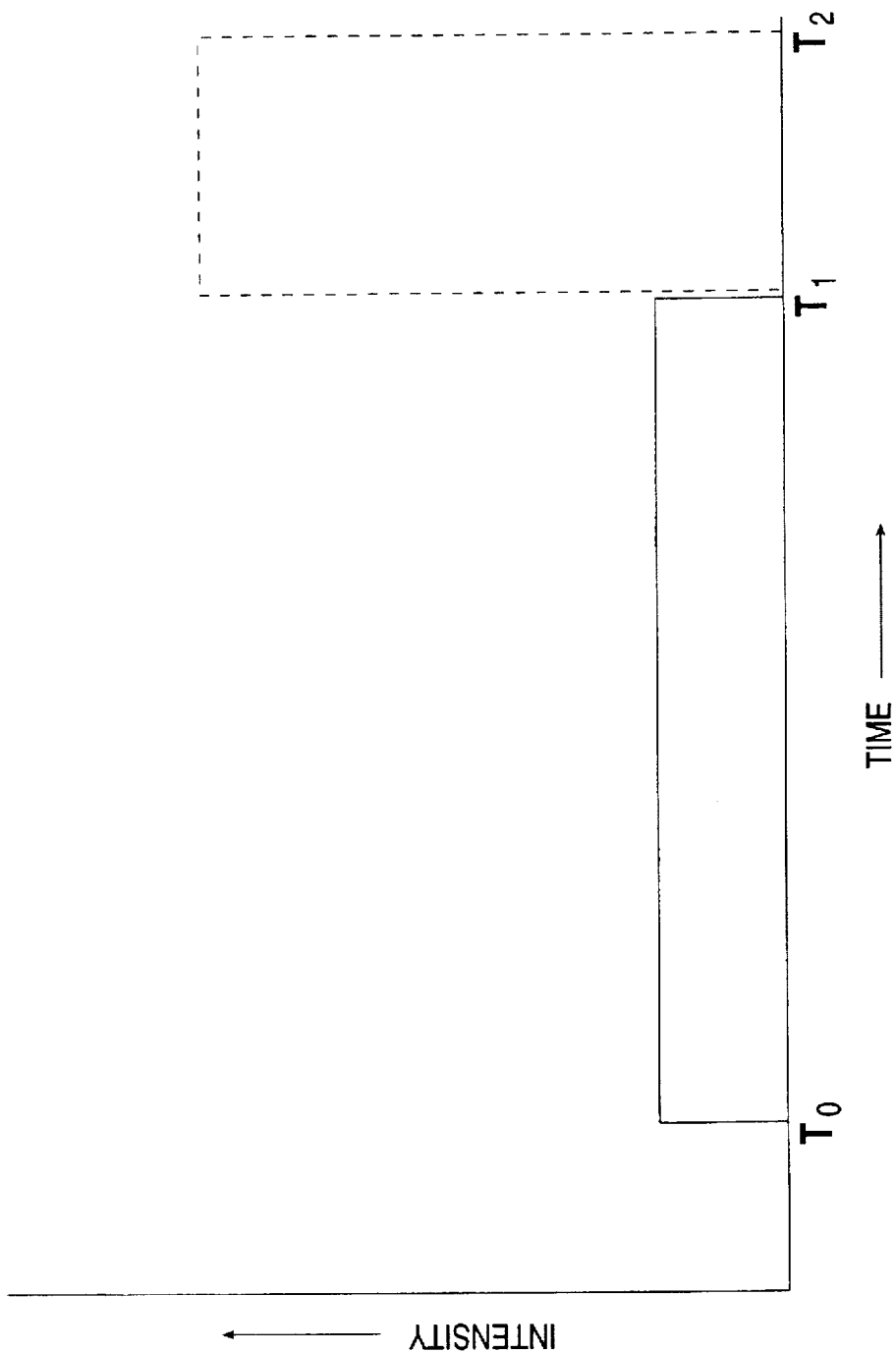
FIG. 6 shows a pulse schedule for the device of FIG. 5.

FIG. 5 is a schematic diagram of a variant of the device of FIG. 3. In the device of FIG. 5, a movable mirror 40 is provided to deflect light passed by shutter 32 to a fixed mirror 41 and a monochromator 42. The device of FIG. 5 generates pulses according to the pulse schedule of FIG. 6, in which, again, the solid line represents a broad-band pulse and the dashed line represents a monochromatic pulse. At time $T_0$, with mirror 40 withdrawn, shutter 32 is opened, allowing broad-band light 14 to pass through an attenuation filter 44 and thence to the target and the surrounding tissue. Like white region 36 of filter 34, attenuation filter 44 attenuates all wavelengths to substantially the same degree, to provide a broad-band pulse of the proper duration and intensity to heat the target and the surrounding tissue to about 60° C. At time $T_1$, mirror 40 is moved into place, terminating the broad-band pulse, and, deflecting broad-band light 14 so that it passes, via mirror 41, through monochromator 42, thereby initiating the monochromatic pulse. Thus, the monochromatic pulse starts substantially immediately after the termination of the broad-band pulse. Monochromator 42 passes on to the target only a narrow spectral band of light centered on a wavelength of 585 nanometer. At time $T_2$, shutter 32 closes, terminating the monochromatic pulse.

While the invention has been described with respect to a limited number of embodiments, it will be appreciated that many variations, modifications, and other applications of the invention may be made.

What is claimed is:

1. A method of selective photothermolysis of a target within surrounding tissue, comprising the steps of:
   (a) heating the target and the surrounding tissue together above normal body temperature; and
   (b) heating the target further to between about 70° C. and about 80° C.

2. The method of claim 1, wherein said heating of the target and the surrounding tissue together above normal body temperature is to a temperature of between about 55° C. and about 65° C.

3. The method of claim 1, wherein said heating of the target and the surrounding tissue together above normal body temperature is effected by using electromagnetic radiation.

4. The method of claim 3, wherein said electromagnetic radiation is microwave radiation.

5. The method of claim 3, wherein said electromagnetic radiation is pulsed.

6. The method of claim 5, wherein said electromagnetic radiation is generated by a source including at least one lamp.

7. The method of claim 6, wherein said pulsing is effected using a mechanism including at least one shutter.

8. The method of claim 1, wherein said further heating of the target is effected by using pulsed, substantially monochromatic electromagnetic radiation.

9. The method of claim 8, wherein said electromagnetic radiation is characterized by a wavelength of between about 570 nanometers and about 610 nanometers.

10. The method of claim 8, wherein said electromagnetic radiation is generated by a laser.

11. The method of claim 8, wherein said electromagnetic radiation is generated by a system including:
   (a) at least one lamp; and
   (b) a mechanism for wavelength selection.

12. The method of claim 11, wherein said mechanism for wavelength selection includes at least one filter.

13. The method of claim 11, wherein said mechanism for wavelength selection includes at least one monochromator.

* * * * *